US010098614B2

(12) United States Patent
Haugaard et al.

(10) Patent No.: US 10,098,614 B2
(45) Date of Patent: Oct. 16, 2018

(54) HIGH DYNAMIC RANGE ULTRASOUND FLOW IMAGING SYSTEM

(71) Applicant: B-K Medical Aps, Herlev (DK)

(72) Inventors: Per Haugaard, Skovlunde (DK); Gert Seerup, Hilleroed (DK)

(73) Assignee: B-K Medical Aps, Herlev (DK)

( * ) Notice: Subject to any disclaimer, the term of this patent is extended or adjusted under 35 U.S.C. 154(b) by 585 days.

(21) Appl. No.: 14/810,653

(22) Filed: Jul. 28, 2015

(65) Prior Publication Data

US 2017/0027547 A1    Feb. 2, 2017

(51) Int. Cl.
*A61B 8/08* (2006.01)
*A61B 8/06* (2006.01)
*A61B 8/00* (2006.01)
*G01S 15/89* (2006.01)
*G01S 7/52* (2006.01)

(52) U.S. Cl.
CPC .............. *A61B 8/5207* (2013.01); *A61B 8/06* (2013.01); *G01S 7/52034* (2013.01); *G01S 15/8915* (2013.01); *G01S 15/8988* (2013.01); *A61B 8/4483* (2013.01); *A61B 8/488* (2013.01)

(58) Field of Classification Search
CPC ......... A61B 8/06; A61B 8/4483; A61B 8/488; A61B 8/5207; G01S 15/8915; G01S 15/8988; G01S 7/52034
See application file for complete search history.

(56) References Cited

U.S. PATENT DOCUMENTS 6,859,659 B1 * 2/2005 Jensen ................ G01S 15/8984
                                                        342/108
9,538,987 B2 * 1/2017 Hoctor ................. A61B 8/4477

\* cited by examiner

*Primary Examiner* — Michael Rozanski
(74) *Attorney, Agent, or Firm* — Anthony M. Del Zoppo, III; Daugherty & Del Zoppo Co., LPA

(57) ABSTRACT

An ultrasound imaging system includes an ultrasound transducer that receives an echo signal generated in response to an ultrasound signal transmitted by the system interacting with a moving material. Receive circuitry processes the echo signal and produces an electrical signal indicative thereof. Front end electronics amplify and digitize the electrical signal producing M-bit RF data. A beamformer that processes the M-bit RF data and generates N-bit high dynamic range beamformed data. N is greater than M. The system further includes pre-processing circuitry that converts the N-bit data RF to 2×K-bit I/Q data. K is less than M. A velocity processor determines a phase estimate of the moving material from the I/Q data. A rendering engine visually presents the phase estimate.

31 Claims, 4 Drawing Sheets

HIGH DYNAMIC RANGE ULTRASOUND FLOW IMAGING SYSTEM

TECHNICAL FIELD

The following generally relates to ultrasound imaging and particularly to flow imaging such as color flow imaging, vector velocity imaging and/or other flow imaging.

BACKGROUND

Ultrasound imaging provides a real-time image with information about the interior of an object or a subject such as tissue, organs, etc. In addition, ultrasound imaging can visualize the flow inside of a cavity in real-time such as the flow of blood cells inside of blood vessels. Conventional Color Flow Mapping (CFM) is one approach to estimate and visualize the flow inside blood vessels. In one instance, the CFM image is super-imposed on a black-and-white (B-mode) image that shows the tissue structures. The CFM image can be realized efficiently and made feasible using a low-cost velocity estimator.

CFM imaging has typically been limited to a smaller region of interest (ROI) of the whole image view relative to the B-mode image in order to achieve high enough frame-rates. This frame-rate issue has been addressed in current ultrasound systems utilizing parallel data acquisition. However, even with full depth color flow view and good frame-rates, is it an obstacle to actually visualize unbroken blood-flow information in the full penetration depth with a conventional color flow velocity estimator, e.g., at least due to very large variation in the dynamic range of the input signal.

The gain for Doppler-based systems may not be controlled as a time gain compensation (TGC) as for B-mode, which in general is used to compensate for the depth dependent tissue attenuation, as time-dependent gain changes will introduce false velocity artifacts into the CFM image. Hence, when the user-adjustable gain setting is high (e.g. 60 dB), the flow from the weakest signal at the bottom of the image becomes visible, but the flow from the strong signal at the skin-surface close to the transducer breaks up or disappears. When the gain setting is low (e.g. 40 dB), the flow at the top of the image reappears but the flow at the bottom disappears.

This is illustrated in FIGS. 1 and 2, which show an ultrasound transducer array 102 next to the skin 104 and vascular structure 106 in the field of view 108. The vascular structure 106 includes first vascular structure 110 in the near field 112 (from just below the surface to e.g. 8 cm) and second vascular structure 114 in the far field 116 (to e.g. 18 cm). FIG. 1 shows an example of lower gain, where only the first vascular structure 110 in the near field 112 (the shaded structure) is properly visualized. FIG. 2 shows an example of higher gain, where only the second vascular structure 114 in the far field 116 (the shaded structure) is properly visualized.

A reason for the above is the dynamic range of the CFM processing, which is limited to operating on complex samples of 2×16-bit fixed-point values (integer values). This is required partly to restrict the requirements for access to fast temporal storage (central processing unit (CPU), digital signal processor (DSP) or graphics processing unit (GPU) cache memory) resources. Calculating a full-view frame of CFM for display may require 10 MB (Megabytes) of temporal data, which easily becomes an issue with respect to the available resources. Unfortunately, doubling this by simply going from 2×16-bit fixed-point to 2×32-bit floating-point will have a significant impact on performance (frame rate). A vector flow imaging (VFI) system may require up to three (3) times the resources, and, thus, will have an even greater significant impact on the performance.

SUMMARY

Aspects of the application address the above matters, and others.

In one aspect, an ultrasound imaging system includes an ultrasound transducer that receives an echo signal generated in response to an ultrasound signal transmitted by the system interacting with a moving material. Receive circuitry processes the echo signal and produces an electrical signal indicative thereof. Front end electronics amplify and digitize the electrical signal producing M-bit RF data. A beamformer that processes the M-bit RF data and generates N-bit high dynamic range beamformed data. N is greater than M. The system further includes pre-processing circuitry that converts the N-bit data RF to 2×K-bit I/Q data. K is less than M. A velocity processor determines a phase estimate of the moving material from the I/Q data. A rendering engine visually presents the phase estimate.

In another aspect, a method includes generating N-bit high dynamic range beamformed data from M-bit RF ultrasound data, wherein N is greater than M, converting the N-bit high dynamic range beamformed data to 2×K-bit I/Q data, wherein K is less than N, generating a flow estimate for flowing material from the I/Q data, and displaying the flow estimate.

In another aspect, a computer readable storage medium is encoded with computer readable instructions. The computer readable instructions, when executed by a processor, causes the processor to: generate high dynamic range beamformed data from ultrasound data, generate a flow information for flowing material represented in the ultrasound data from the high dynamic range beamformed data, and display the flow information.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 3:
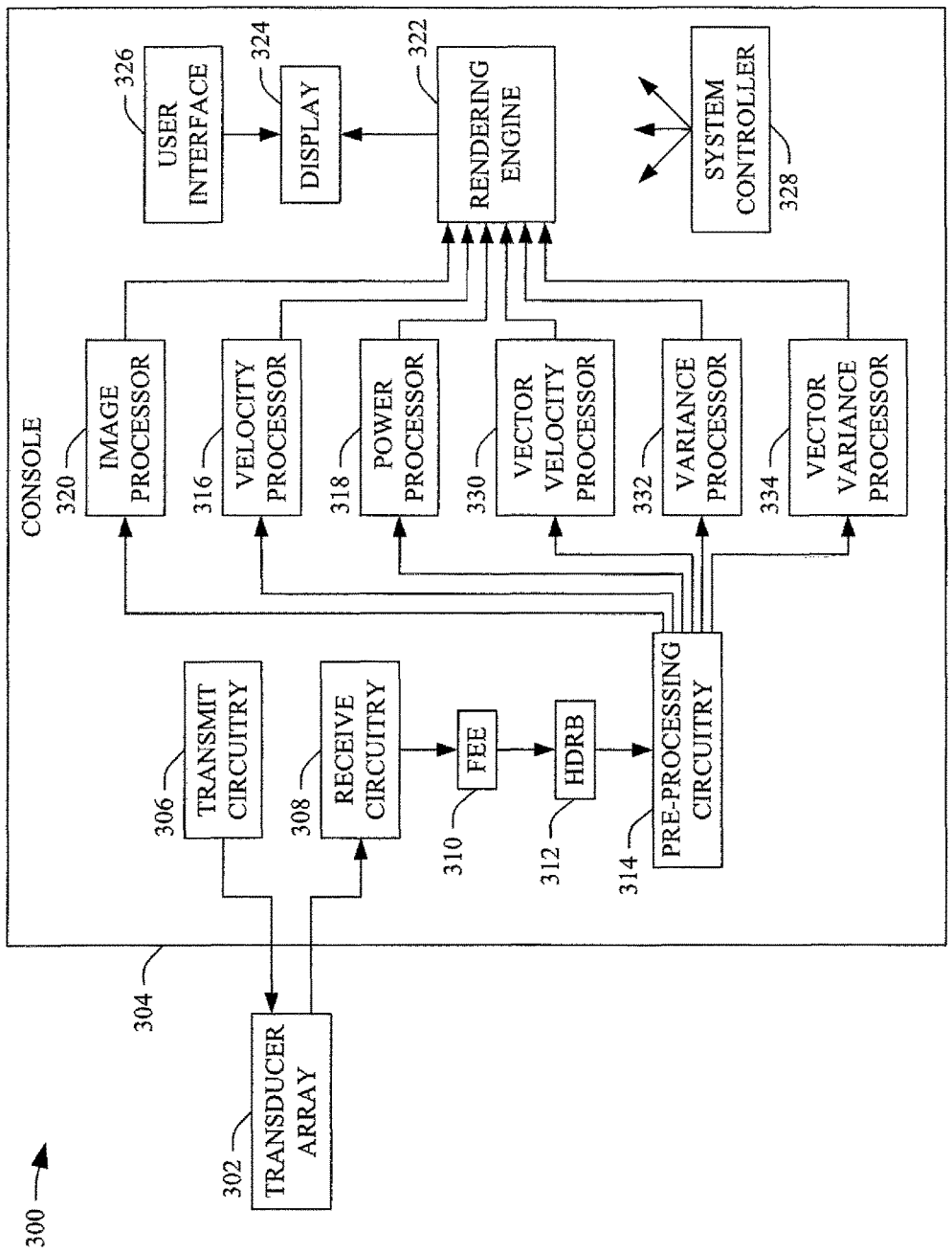
FIG. 3 schematically illustrates an example ultrasound imaging system including at least front end electronics, a high dynamic range beamformer, pre-processing circuitry, a velocity processor, a power processor and a vector velocity processor.

FIG. 3 schematically illustrates an example ultrasound imaging system 300.

The ultrasound imaging system 300 includes a transducer array 302 that interfaces with a console 304 through suitable wire and/or wireless interfaces. The ultrasound imaging system 300 can be part of a portable system on a stand with wheels, a system residing on a tabletop, and/or other system in which the transducer array 302 is housed in a probe or the like, and the console 304 is housed in an apparatus separate therefrom. In another instance, the transducer array 302 and the console 304 can be housed in a same apparatus such as within a hand-held ultrasound scanner.

The transducer array 302 converts an electrical signal to an ultrasound pressure field and vice versa. The one or more transducer elements are selectively excited via a set of electrical pulses (or a pulsed signal), which cause at least a sub-set of the transducer elements to transmit ultrasound signals, e.g., into an examination or scan field of view. Examples of suitable arrays include 64, 128, 192, 256, and/or other elements arrays, including larger and smaller arrays. The array can be linear, curved, and/or otherwise shaped, fully populated, sparse and/or a combination thereof, etc.

The console 304 includes transmit circuitry 306 configured to generate the set of pulses conveyed to the transducer array 302. The pulses can be conveyed via hardwire and/or wirelessly. For velocity estimation, the transmit circuitry 306 is configured to transmit a predetermined number M (where M is an integer) of pulses in order to receive back echoes acquired in a same beam-direction versus time at a pulse repetition frequency (PRF) of 5-20 kHz. The time domain defined by the PRF is the PRF-time dimension.

The console 304 further includes receive circuitry 308 configured to receive a set of echo signals (ultrasound pressure field) generated in response to the transmitted ultrasound signals and generate analog electrical signals indicative thereof. The set of echo signals, in one instance, are generated in response to the transmitted ultrasound signals interacting with structure such as blood flowing in a portion of a vessel and/or organ cells in a region of interest in the scan field of view and/or other structure.

The console 304 further includes a front end electronics (FEE) 310, a high dynamic range beamformer (HDRB) 312 and pre-processing circuitry 314. A described in greater detail below, the FEE 310 processes the analog output of the receive circuitry 308, generating digital beams of N-bit RF-data (where N is an integer) for flow imaging. The HDRB 312 processes (delays, weights and sums) the output of the FEE 310, producing higher bit RF-data (beamformed scan-lines). The pre-processing circuitry 314 processes the higher bit beamformed scan-lines, reducing the number of bits and converting the reduced bit RF data to I/Q data.

The console 304 further includes a velocity processor 316, includes a power processor 318, and an image processor 320. As described in greater detail below, the velocity processor 316, which includes multiple stages, processes the output of the pre-processing circuitry 314 and produces velocity (or phase) estimates. The power processor 318, which includes multiple stages, processes the output of the pre-processor 314 and produces power estimate. The image processor 320 processes the output of the pre-processor 314 and produces ultrasound images.

The console 304 further includes a vector velocity processor 330, a variance processor 332 and a vector variance processor 334. The vector velocity processor 330 processes the output of the pre-processor 314 and produces direct and magnitude estimates. The variance processor 332 processes the output of the pre-processor 314 and produces data indicating a level of a variance of the velocity estimate (e.g. flow turbulence) of the input. The vector variance processor 334 processes the output of the pre-processor 314 and produces data indicating the level and a direction of the flow turbulence.

In a variation, at least one of but not all of the velocity processor 316, the power processor 318, the vector velocity processor 330, the variance processor 332 and/or the vector variance processor 334 is omitted.

Figure 1:
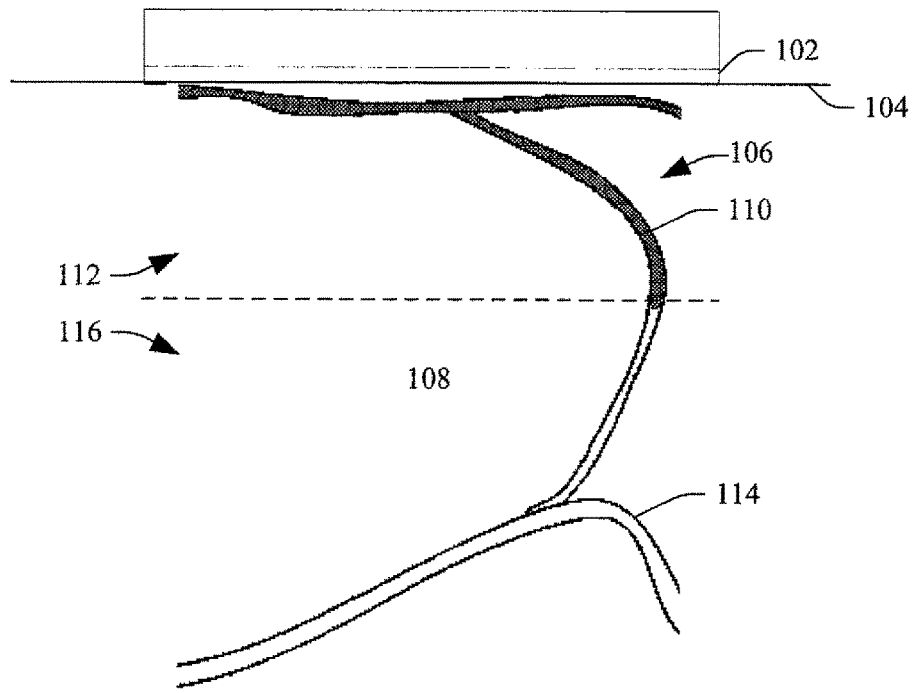
FIG. 1 illustrates an example of the prior art flow imaging where only the blood flow in the vessels near to the transducer is properly visualized.
Figure 2:
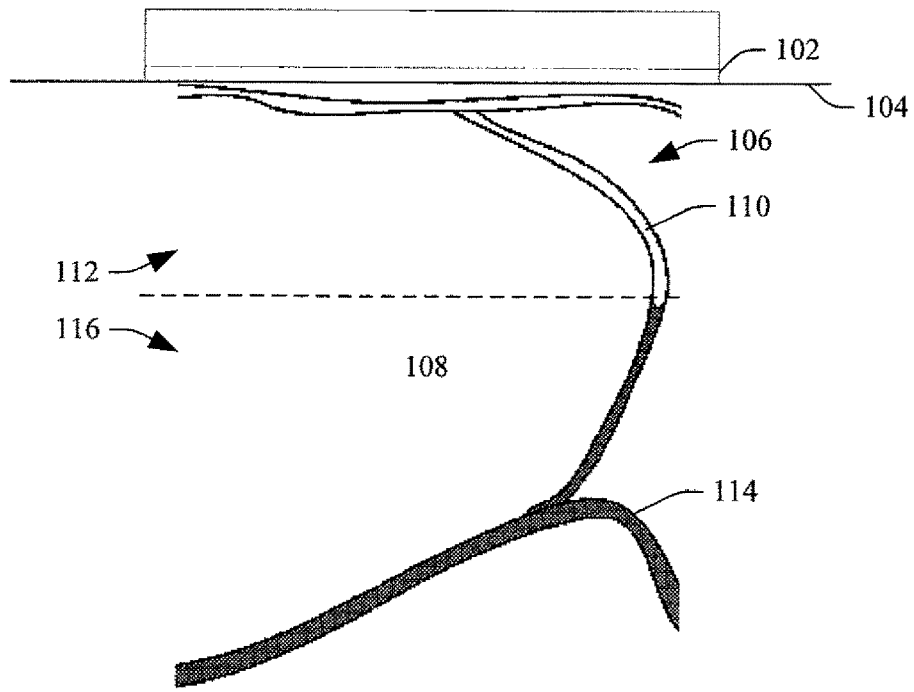
FIG. 2 illustrates an example of the prior art flow imaging where the only the blood flow in the vessels far from the transducer is properly visualized.

With the processing described herein, flow in vascular structure (104 of FIG. 1) in both the near field (112 of FIG. 1) and far field (116 of FIG. 1) can be concurrently properly visualized without weak signals becoming invisible and/or without strong signals breaking up or disappearing. Furthermore, the processing described herein does not increase the requirements for access to fast temporal storage (CPU, DSP or GPU cache memory) resources as would be the case if the acquired data were double, tripled, etc. For example, with the approach described herein, the data need not be doubled going from 2×16-bit fixed-point to 2×32-bit floating-point for CFM or tripled for VFI, which would degrade performance.

Figure 4:
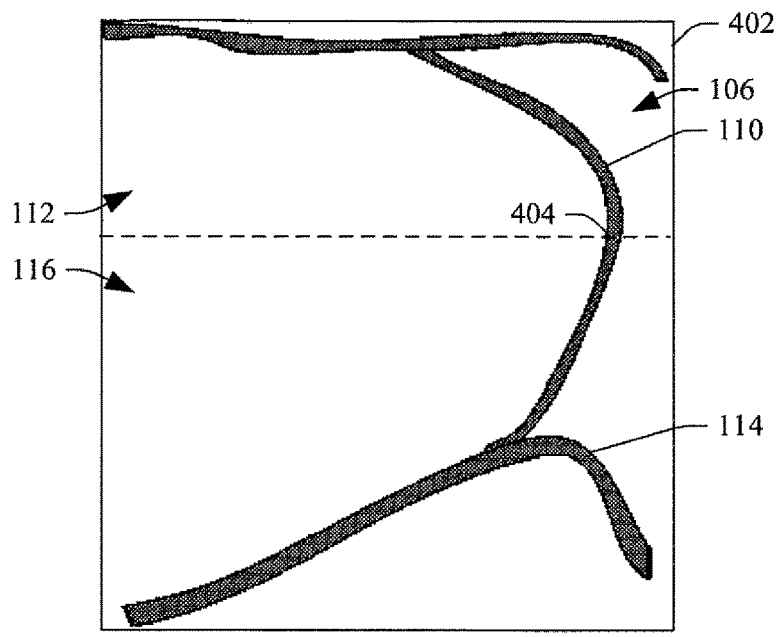
FIG. 4 illustrates an example where blood flow in the vessels in the near and the far fields is properly visualized.

The console 304 further includes a rendering engine 322 and a display 324. The rendering engine 322 visually presents, via the display 324, the image generated by the image processor 320 with flow information generated by the velocity processor 316 superimposed there over. FIG. 4 shows a B mode image 402 with flow imaging information 404 (the gray shading inside of the vascular structure 114) in both the near field 112 (the vascular structure 110) and the far field 116 (the vascular structure 114). Optionally, power information generated by the power processor 318 and/or vector velocity information generated by the vector velocity processor 330 can be visually presented. Indicia such as color, arrows, etc. can be used to show magnitude and/or direction.

The console 304 further includes a user interface (UI) 326 with one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 300. The console 304 further includes a controller 328 configured to control one or more of the components of the console 304, the transducer array 302, and/or other device. Such control can be based on a mode of operation (e.g., B-image+flow (CFM, VFI, etc.) mode, etc.) and/or otherwise.

In one instance, one or more of the components of the console 304 can be implemented via one or more processors (CPU, microprocessor, controller, etc.) executing one or more computer readable instructions encoded or embedded on non-transitory medium computer readable storage medium such as physical memory or other non-transitory medium. Additionally or alternatively, at least one of the instructions can be carried by a carrier wave, a signal, or other transitory medium, with the one or more processors executing the at least one of the instructions to implement the one or more of the components.

Figure 5:
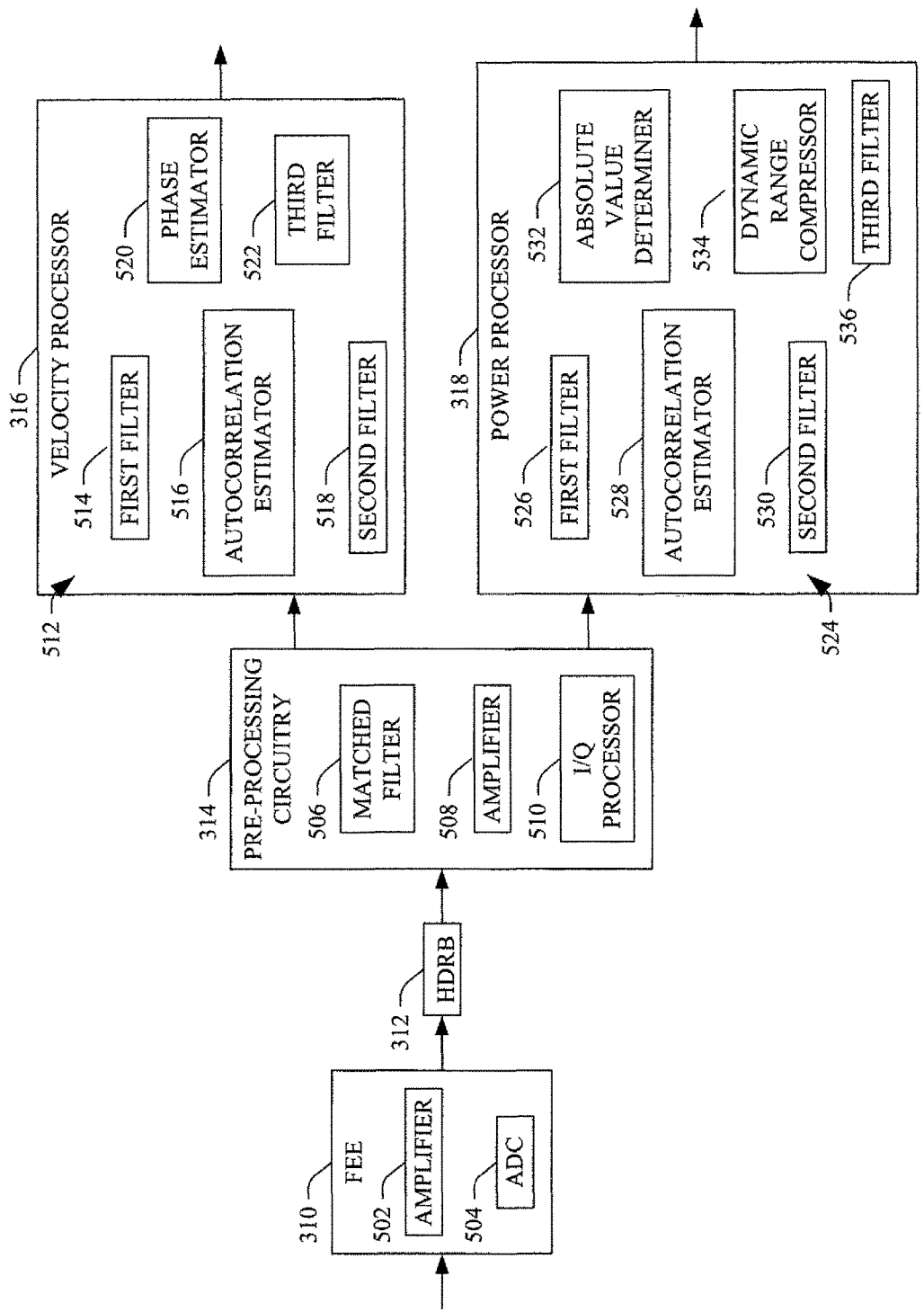
FIG. 5 schematically illustrates examples of the front end electronics, the high dynamic range beamformer, the pre-processing circuitry, the velocity processor, and the power processor.

FIG. 5 shows an example of the FEE 310, the HDRB 312, the pre-processing circuitry 314, the velocity processor 316 and the power processor 318. For sake of brevity and clarity, this example is described for a specific data format (i.e., number of bits of input and output data). However, data formats are also contemplated herein.

The FEE 310 includes an amplifier 502 configured to amplify the set of electrical signals from receive circuitry 308. In one instance, this includes amplifying the set of electrical signals from a micro-volt level to the volt level. Generally, a gain of the amplifier 502 is configured high enough to amplify weak signals originating from echoes from moving blood particles (e.g., those in the far field) and not cause clipping of the signal (e.g., those in the near field), which may otherwise render the input signals not well suited for subsequent processing and display.

The FEE 310 further includes an analog-to-digital (ADC) 504 for each input channel (e.g., 192 ADC's for 192 input channels). In this example, a dynamic range of the ADC 504 is 16-bits. In generally, the dynamic range of the ADC 504 can be 8 to 16-bits. Data for velocity estimation are acquired by sampling at a sample frequency (FS) of e.g. 60 MHz versus time (scan-line depth). The time-dimension defined by FS is the FS-time dimension.

The HDRB 312 processes the output of the FEE 310. In one instance, this includes applying time delays to the output, weighting the output, and summing the delayed and weighted output, and/or otherwise beamforming signals. The HDRB 312 is configured to produce one or more beams for one or more scan-lines per shot. The HDRB 312 is configured to produce an output of higher bit RF data, e.g., generating 24-bit beamformed data per channel. In this example, the HDRB 312 has a 16-bit input and a 24-bit output. However, the HDRB 312 can have, for example, 8 to 2048 input channels, for example, 192 input channels, and the output can range from 16 to 32 bits.

The pre-processing circuitry 314 includes a matched filter 506. The matched filter 506 is configured to operate on the output of the HDRB 312. The matched filter 506 matches the output with the expected receive-echo pulse shape (bandwidth). In a variation, the matched filter 506 is omitted.

The pre-processing circuitry 314 further includes an amplifier 508 configured to amplify the output of the HDRB 312 or the matched filter 506. The amplifier 508 may amplify the signal such that the signal is clipped (over-steered) while ensuring that the weakest beam-formed signal is present. This allows for reducing the 24-bit beamformed data to 16-bits. Reducing the data as such reduces the requirements for processing and fast temporal storage. For example, processing 24-bit data at 40-60 MSps (Mega Samples per Second) would require processing and fast temporal storage resources beyond what is needed and available in state of the art ultrasound systems.

The pre-processing circuitry 314 further includes an I/Q processor 510 configured to convert the 16-bit RF-data to 16-bit I/Q data. This can be achieved, for example, using a Hilbert Transform filter, a combination of a Complex-Demodulation Band Pass Filter and optional Decimation, and/or otherwise.

The velocity processor 316 includes a plurality of processing stages 512.

A first processing stage includes a first filter 514 configured to (high-pass) filter along the PRF-time dimension to remove high-amplitude stationary signals and high-amplitude signals from slow moving objects like the walls of the blood vessels. A suitable filter is a Wall filter and can be based on a FIR filter, an IIR filter, an arbitrary matrix filter, typically described with unit-normalized 16-bit fixed-point coefficient to realize narrow stop-band attenuation comparable to the dynamic range of the input signal and unity gain in the pass-band, etc.

The first filter 514 is configured to, without loss; filter both the weakest input signal and the heavily over-steered input signal. The output of the first filter 414 corresponds to a dynamic range of, e.g., 2×32-bit (2×192 dB), but the blood-flow signal output of the first filter 514 does not have a precision or a dynamic range of 32-bit. After the first filter 514 has removed the high-amplitude part, the output signal is dominated by the input blood-flow signal with unchanged dynamic range at 2×16 bit. To handle a heavy over-steered input signal, the first filter 514 outputs its impulse response undistorted.

For a filter with a pass-band ripple of up to 6 dB, an extra output bit is required, forming a high dynamic resolution filter with an output of 2×17 bit (102 dB). In one instance, the intended precision to visualize the flow signal on the final display is not more than 8-bit. For this, a 14-bit floating-point data format consisting of an 8-bit mantissa, a 5-bit exponent and a 1-bit sign is required to represent the 2×102 dB output signal from the high dynamic resolution filter. The instantaneous dynamic range of the blood-flow signal embedded in the input signal is typically much less than this.

A second processing stage includes an autocorrelation estimator (ACE) 516 configured to compute an AC estimation along the PRF-time dimension. For high dynamic resolution velocity estimation, a suitable autocorrelation handles the weakest input signal and the heavily over-steered input signal. To handle the weakest input signal, the ACE 516 produces an output without loss, corresponding to 2×32-bit (192 dB). To handle the heavily over-steered input signal for up to M shot in an acquisition package, there is an additional log 2(M−1) bit, where log 2( ) is the base-2 logarithm.

For M=16 shots, there is an additional 4 bit for the ACE 516 by itself plus the extra 1 bit from the first filter 514, resulting in a 2×37-bit (222 dB) dynamic range output from the ACE 516. A 15-bit floating-point data format of 8-bit mantissa, a 6-bit exponent and a 1-bit sign is required to represent the 2×222 dB output signal from the ACE 516. A normalized mantissa format can be used, which may save one bit while using extra levels of the exponent. This reduces the output of the ACE 516 to a 14-bit floating-point data format of 7-bit normalized mantissa, a 6-bit exponent and a 1-bit sign.

In general, the output of the ACE 516 can be 15-bit to 16-bit floating-point data format consisting of an 8-bit to 9-bit mantissa, a 6-bit to 8-bit exponent and a 1-bit sign; 14-bit to 16-bit floating-point data format consisting of an 7-bit to 9-bit normalized or not normalized mantissa, a 6-bit to 8-bit exponent and a 1-bit sign; or 16-bit floating-point data format consisting of an 7-bit to 8-bit normalized or not normalized mantissa, a 7-bit to 8-bit signed exponent and a 1-bit sign.

A third processing stage includes a second filter 518 configured to average the output of the ACE 516. In one instance, the averaging is done in the FS-time dimension, over several acquisition packages, in the lateral beam dimension, and/or in the temporal frame dimension in order to improve the blood-flow sensitivity or resolution further. The acquisition packages might consist of data from fully overlapping transmit/receive beam-directions or partially overlapping transmit/receive beam direction. The case where blood-flow sensitivity can be further improved is when the 8-bit mantissa in the output from the ACE 516 maybe dominated by noise wherein a weaker blood-flow signal is embedded. Hence the output of the second filter 518 does not require higher dynamic range for representation. In a variation, the second filter 518 is omitted.

A fourth processing stage includes a phase estimator (PE) 520 configured to estimate a velocity, or compute a phase estimation by an arctangent operation. The arctan(I,Q) estimates the angle (phase) of the I/Q-vector in the complex plane. The first step of the arctan operation is to normalize the input to the largest of its input arguments and thereby eliminating the exponent and hence the floating-point data format altogether, reducing the arctan to a conventional 8-bit operation, which can be implemented efficiently using Taylor-series approximation, a short Look Up Table (LUT), a combination and/or otherwise. For example, the PE 520 can estimate phase by computing an arctangent approximation based on a Taylor-series and/or LUT Taylor-series approximation on the 7-bit to 16-bit floating-point input with an output of 7-bit to 16-bit or more.

A fifth processing stage includes a third filter 522 configured to average the velocity (phase) estimates. The averaging may be done in the FS-time dimension, over several acquisition packages, in the lateral beam direction, and/or in the temporal frame dimension in order to improve the blood-flow sensitivity and/or resolution further. The acquisition packages might consist of data from fully overlapping transmit/receive beam-directions or partially overlapping transmit/receive beam direction. The case where blood-flow sensitivity can be further improved is when the 8-bit velocity data is dominated by noise wherein a weaker blood-flow signal is embedded. In a variation, the third filter 522 is omitted.

The vector velocity processor 330 is substantially similar the velocity processor 316, except that it includes a vector flow determiner that computes a vector velocity. An example of a suitable approach for determining axial and lateral velocity components based on autocorrelation is described in U.S. Pat. No. 6,859,659 B1, filed on Nov. 9, 2001, and entitled "Estimation of Vector Velocity," which is incorporated herein by reference in its entirety. Other approaches for determining the axial (Vz) and lateral (Vx) velocity components and/or a transverse component Vy, which is transverse to Vx and Vz, are also contemplated herein. The output of the vector velocity processor 330 can be, for example, 16-bit floating-point data format consisting of a 7-bit to 8-bit normalized or not normalized mantissa, a 7-bit to 8-bit signed exponent and a 1-bit sign.

The variance processor 332 is substantially similar the velocity processor 316, except that it includes a variance estimator in place of the phase estimator 520. The input to the variance processor 332 is the I/Q data signal and the output is a 5 to 16 bit signal indicating a level of a variance of the velocity estimate (e.g. flow turbulence) of the input. The input to the vector variance processor 334 is the I/Q input data and the output is a 5 to 16 bit signal indicating a level of a vector-variance of the vector-velocity estimate (e.g. flow turbulence) of the input.

The power processor 318 includes a first filter 526, an autocorrelation estimator 528, a second filter 530 and a third filter 536, which function substantially similar to or the same as the first filter 514, the autocorrelation estimator 516, the second filter 518 and the third filter 522.

The power processor 318 further includes an absolute value determiner (AVD) 532 configured to derive an absolute value (e.g., via a Pythagoras operation) of the output of the ACE 528 or the second filter 530, resulting in a power output in a 14-bit floating-point data format of 8-bit mantissa and 6-bit exponent representing the 2×216 dB output. In general, the power output can be 14-bit to 16-bit floating-point data format of 8-bit to 10-bit mantissa, and 6-bit to 8-bit exponent. Using a normalized mantissa format, this can be reduced to a 13-bit floating-point data format of 7-bit normalized mantissa and 6-bit exponent. The power processor 318 can be based on a dedicated high dynamic range power estimator of the input acquisition data package or based on the output of the ACE 528.

A dynamic range compressor (DRC) 534 is configured to map the output of the AVD 532 to a predetermined (e.g., 8-bit) display precision. This can be done, e.g., by a logarithmic (log)-based dynamic range compression with control parameter range for the input dynamic range setting and/or gain for an overall gain setting. By applying a log function after a square-root operation of the Pythagoras operation, the square-root operation can be eliminated and DRC can be reduce to a log estimation only. A log of a floating-point data format is essentially log of just the mantissa, which further reduces the log to an 8-bit operation, which can be implemented effectively using a short LUT and/or otherwise. By way of non-limiting example, the DRC 534 can compute a logarithm approximation based on a LUT approximation on the 16-bit floating-point input with an output of 16-bit. In general, the input of the DRC 534 can be 7-bit to 16-bit floating-point, and the output of the DRC 534 can be 7-bit to 16-bit or more.

Figure 6:
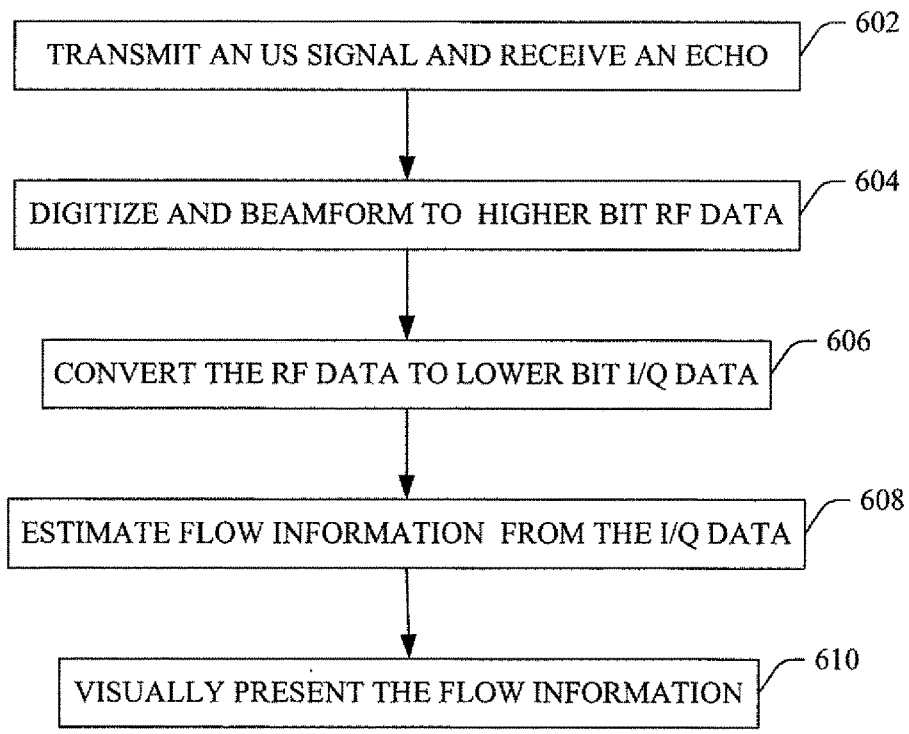
FIG. 6 illustrates an example method in accordance with one or more embodiments herein.

FIG. 6 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 602, an ultrasound signal is transmitted and an echo signal generated in response thereto is received.

At 604, the received signal is digitized into M-bit RF data and then beamformed into N-bit RF-data, where N is greater than M, as described herein and/or otherwise.

At 606, the N-bit data is processed, producing 2×K-bit I/Q data, where K is less than N, as described herein and/or otherwise.

At 608, flow information is estimated for material flow from the I/Q data, as described herein and/or otherwise.

At 610, the flow information is visually presented.

Optionally, a power estimate, a vector velocity estimate, a variance estimate and/or a vector variance estimate can be determined from the I/Q data. Such data can be visualized individually and/or concurrently with the velocity estimate.

By way of non-limiting example, in one instance the velocity processor 316 and the variance processor 332 produce two images simultaneously, one with velocity information, e.g., 1-D bipolar color-scale with black-to-red-shades for positive flow (towards the transducer) and black-to-blue for negative flow (away from the transducer), and one with variance, e.g., 1-D unipolar color-scale with black-to-green for zero to maximum level of variance). These two images are combined into a single image for display, with a 2-D color scale, where the first axis is the velocity-information and the second axis is the variance-information. The more variance in the velocity-estimate, the higher level of the green-color component is added to the pure red/blue-shade component. For vector-variance, where the vector-velocity and vector-variance both are 2-D, the combined image may be e.g. vector-variance color image with an overlay of vector-velocity arrows, or modified arrow-graphics or similar.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
    ultrasound transducer that receives an echo signal generated in response to an ultrasound signal transmitted by the system interacting with a moving material;
    receive circuitry that processes the echo signal and produces an electrical signal indicative thereof;
    front end electronics that amplifies and digitizes the electrical signal, producing M-bit RF data;
    a beamformer that processes the M-bit RF data and generates N-bit high dynamic range beamformed data, wherein N is greater than M;
    pre-processing circuitry that converts the N-bit data to 2×K-bit I/Q data, wherein K is less than M;
    a velocity processor that determines a phase estimate of the moving material from the I/Q data; and
    a display that visually presents the phase estimate.

2. The system of claim 1, wherein M is a value in a range from 8 to 16, and N is a value in a range from 16 to 32.

3. The system of claim 2, wherein M=16 and N=24.

4. The system of claim 1, where the velocity processor comprises:
    a high dynamic range wall filter that filters the I/Q data producing filtered I/Q data; and
    a high dynamic range autocorrelation estimator that processes the filtered I/Q data producing an autocorrelation estimate, wherein the phase estimate is from the autocorrelation estimate.

5. The system of claim 4, wherein the autocorrelation estimate comprises: 15 to 16-bit floating-point data including an 8 to 9-bit mantissa, a 6 to 8-bit exponent, and a 1-bit sign.

6. The system of claim 4, wherein the autocorrelation estimate comprises: 14 to 16-bit floating-point data including a 7 to 9-bit normalized or non-normalized mantissa, a 6 to 8-bit exponent, and a 1-bit sign.

7. The system of claim 4, wherein the autocorrelation estimate comprises: 16-bit floating-point data including a 7 to 8-bit normalized or non-normalized mantissa, a 7 to 8-bit exponent, and a 1-bit sign.

8. The system of claim 4, where the velocity processor comprises:
    an averaging filter that averages the autocorrelation estimate, wherein the velocity processor determines the phase estimate from the average autocorrelation estimate.

9. The system of claim 4, where the velocity processor comprises:
    a phase estimator that estimates the phase estimate by computing an arctangent approximation from the autocorrelation estimate based on at least one of a Taylor-series or a look up table Taylor-series approximation.

10. The system of claim 1, where the velocity processor comprises:
    an averaging filter that averages the phase estimate producing an average phase estimate.

11. The system of claim 1, where the pre-processing circuitry comprises:
    a matched filter that filters the RF data prior to generating the I/Q data.

12. The system of claim 1, further comprising:
    a power estimator that determines a power estimate from the I/Q data, wherein the power estimator comprises:
    a high dynamic range wall filter that filters the I/Q data producing filtered I/Q data; and
    a high dynamic range autocorrelation estimator that processes the filtered I/Q data producing an autocorrelation estimate, wherein the power estimator determines the power estimate from the autocorrelation estimate.

13. The system of claim 12, wherein the autocorrelation estimate comprises: 14 to 16-bit floating-point data including an 8 to 10-bit mantissa, and a 6 to 8-bit exponent.

14. The system of claim 12, wherein the autocorrelation estimate comprises: 13 to 16-bit floating-point data including a 7 to 10-bit normalized or non-normalized mantissa, and a 6 to 9-bit exponent.

15. The system of claim 12, wherein the autocorrelation estimate comprises: 16-bit floating-point data including a 7 to 8-bit normalized or non-normalized mantissa, and a 7 to 8-bit exponent.

16. The system of claim 12, further comprising:
    an absolute value determiner that determines an absolute value from the autocorrelation estimate to estimate the power estimate.

17. The system of claim 16, further comprising:
    a dynamic range compressor configured to compress a dynamic range of the power estimate.

18. The system of claim 17, wherein the dynamic range compressor employs control parameters, including range and gain, which are a function of at least one of time or image depth, to compress the dynamic range of the power estimate.

19. The system of claim 17, wherein the dynamic range compressor computes a logarithm approximation based on a look up table approximation to compress the dynamic range of the power estimate.

20. The system of claim 1, further comprising:
    a vector velocity processor that determines a vector velocity estimate of the moving material from the I/Q data, wherein the vector velocity processor comprises:
    a high dynamic range wall filter that filters the I/Q data producing filtered I/Q data;
    a high dynamic range autocorrelation estimator that processes the filtered I/Q data producing an autocorrelation estimate; and
    a vector flow determiner that estimates the vector velocity estimate based on the autocorrelation estimate.

21. The system of claim 1, further comprising:
    a variance processor that determines a level of flow turbulence from the I/Q data.

22. The system of claim 21, wherein the level of the flow turbulence comprises: 5 to 16-bit data.

23. The system of claim 1, further comprising:
    a vector variance processor that determines a level and a direction of flow turbulence from the I/Q data.

24. The system of claim 23, wherein the level and the direction of the flow turbulence comprises: 5 to 16-bit data.

25. A method, comprising:
  generating, with the processor, N-bit high dynamic range beamformed data from M-bit RF ultrasound data, wherein N is greater than M;
  converting, with the processor, the N-bit high dynamic range beamformed data to 2×K-bit I/Q data, wherein K is less than N;
  generating, with the processor, a flow estimate for flowing material from the I/Q data; and
  displaying, with a display, the flow estimate.

26. The method of claim 25, wherein generating the flow estimate further comprises:
  high pass filtering the I/Q data producing filtered I/Q data;
  estimating a high dynamic range autocorrelation estimate from the high pass filtered I/Q data; and
  generating the flow estimate from the high dynamic range autocorrelation estimate.

27. The method of claim 26, wherein generating the flow estimate further comprises:
  generating a power estimate for the flowing material from the I/Q data.

28. The method of claim 27, wherein generating the power estimate further comprises:
  high pass filtering the I/Q data producing filtered I/Q data;
  estimating a high dynamic range autocorrelation estimate from the high pass filtered I/Q data of the power estimate; and
  determining an absolute value of the high dynamic range autocorrelation estimate of the power estimate to produce the power estimate.

29. The method of claim 28, wherein generating the power estimate further comprises:
  compressing a dynamic range of the power estimate.

30. The method of claim 25, wherein generating the flow estimate further comprises:
  high pass filtering the I/Q data producing filtered I/Q data;
  estimating a high dynamic range autocorrelation estimate from the high pass filtered I/Q data; and
  estimating a vector velocity estimate from the high dynamic range autocorrelation estimate.

31. A non-transitory computer readable storage medium encoded with computer readable instructions, which, when executed by a processor, causes the processor to:
  generate N-bit high dynamic range beamformed data from M-bit RF ultrasound data, wherein N is greater than M;
  convert the N-bit high dynamic range beamformed data to 2×K-bit I/Q data, wherein K is less than N;
  generate a flow estimate for flowing material from the I/O data; and
  display the flow estimate.

* * * * *